I

United States Patent
Yang et al.

(10) Patent No.: US 12,065,679 B2
(45) Date of Patent: Aug. 20, 2024

(54) ASPERGILLUS ORYZAE AND ITS APPLICATION

(71) Applicant: Wenzhou University, Zhejiang (CN)

(72) Inventors: Hailong Yang, Zhejiang (CN); Huabin Zhou, Zhejiang (CN); Zhihan Zheng, Zhejiang (CN); Xiangting Wu, Zhejiang (CN)

(73) Assignee: Wenzhou University, Zhejiang (CN)

( * ) Notice: Subject to any disclaimer, the term of this patent is extended or adjusted under 35 U.S.C. 154(b) by 184 days.

(21) Appl. No.: 17/735,129

(22) Filed: May 3, 2022

(65) Prior Publication Data
US 2023/0357738 A1  Nov. 9, 2023

(51) Int. Cl.
*C12N 1/14* (2006.01)
*C12N 9/30* (2006.01)

(52) U.S. Cl.
CPC .............. *C12N 9/242* (2013.01); *C12N 1/14* (2013.01)

(58) Field of Classification Search
None
See application file for complete search history.

(56) References Cited

PUBLICATIONS

Zheng et al. (Food Chemistry, vol. 432 (2024) 137195.*
Bo Qi-Feng et al., "Progress in research of relationship between intestinal flora regulation and type 2 diabetes" Shanghai Journal of Preventive Medicine, vol. 31, Issue 3, Mar. 2019, with English abstract, pp. 242-246.
Zeng Ya et al., "Current research developments of the therapeutic drugs for type 2 diabetes based on visual analysis" , Journal of Shenyang Pharmaceutical University, vol. 36, Issue 8, Aug. 2019, with English abstract, pp. 739-749.
Ding Haomiao et al., "Inhibition of Polysaccharide Fraction of Sargassum fusiforme on the α-glucosidase", Journal of Nuclear Agricultural Sciences, vol. 33, Issue 2, Feb. 2019, with English abstract, pp. 297-304.
Konstantinos Papoutsisa et al., "Fruit, vegetables, and mushrooms for the preparation of extracts with α-amylase and α-glucosidase inhibition properties: A review", Food Chemistry, vol. 338, Sep. 2020, pp. 1-17.
Yuan Hong et al., "Screening and characterization of potential α-glucosidase inhibitors from Cercis chinensis Bunge fruits using ultrafiltration coupled with HPLC-ESI-MS/MS", Food Chemistry, vol. 372, Mar. 2020, pp. 1-7.

* cited by examiner

*Primary Examiner* — Richard G Hutson
(74) *Attorney, Agent, or Firm* — JCIPRNET

(57) ABSTRACT

An *Aspergillus oryzae* and its application belong to the field of microbiology and food processing technology. The present application, on the one hand, provides an *Aspergillus oryzae* (WZ-212), on the other hand, provides this *Aspergillus oryzae* in application of enhancing the inhibitory activity of α-glucosidase by grapefruit peel and the method of application. Using the *Aspergillus oryzae* of this application to treat grapefruit peel, the inhibition of α-glucosidase activity by grapefruit peel extract was significantly enhanced, and the process is simple, low cost, which is easy to achieve industrial production.

2 Claims, 3 Drawing Sheets

Specification includes a Sequence Listing.

ASPERGILLUS ORYZAE AND ITS APPLICATION

BACKGROUND

Technical Field

The present invention belongs to the field of microbiology and food processing technology, and specifically relates to an *Aspergillus oryzae* and its application, especially relates to this *Aspergillus oryzae* in the application of enhancing the inhibition of α-glucosidase activity by grapefruit peel.

Description of Related Art

Diabetes Mellitus is one of the chronic diseases with the fastest growing rate in China, there were 425 million adults (20-79 years old) with diabetes mellitus worldwide in 2017, and China is accounting for a quarter of the total, making it the country with the largest number of diabetics, wherein mainly type 2 diabetics (Bo Q F, Chen Y Y, 2019. Progress in research of relationship between intestinal flora regulation and type 2 diabetes. Shanghai Journal of Preventive Medicine, 31(3): 242-246). At present, there are four main types of drugs that have been marketed for the treatment of type 2 diabetes mellitus, including sulfonylurea insulin promoting drugs, biguidine hypoglycemic drugs, thiazolidinedione insulin-sensitizing drugs and α-glucosidase inhibiting drugs (Zeng Y, Xing B, Zhang Y, Xiao K, Liang J K, Jiang X W. Current research developments of the therapeutic drugs for type 2 diabetes based on visual analysis. Journal of Shenyang Pharmaceutical University, 2019, 36(8): 739-749). Representative drugs used to inhibit α-glucosidase activity include acarbose, voglibose, miglitol, etc., which has good efficacy, but long-term use has the risk of causing liver and kidney damage in humans (Ding H S, Sun T, Xia P K, Tang Q, Wang Z H, Wang C S, Chen H M, Qian G Y, 2019. Inhibition of Polysaccharide Fraction of Sargassum fusiforme on the α-glucosidase. Journal of Nuclear Agricultural Sciences, 33(2): 297-304).

Related studies have shown that many functional substances such as anthocyanins, flavonoids, phenolic acids, saponins, terpenes, fatty acids and alkaloids can be obtained from many plants, and most of these substances have good α-glucosidase inhibitory activities (Hong Y, Liao X Y, Chen Z L. Screening and characterization of potential alpha-glucosidase inhibitors from Cercis Chinensis Bunge fruits using ultrafiltration coupled with HPLC-ESI-MS/MS. Food Chemistry, 2022, 372: 131316), therefore, plant extracts have the potential to be used as existing drug substitutes, and the selection of plant extracts of natural origin for daily prevention and treatment of diabetes mellitus is an effective way to reduce the side effects of drugs.

Grapefruit products are very popular all over the world because of their delicious taste and good nutritional value. However, grapefruit is generally eaten directly or made into juice, and its by-products including grapefruit peel and seeds are treated as waste, and these by-products account for approximately 50% of fresh grapefruit peel. Grapefruit peel contains a large number of phenolic compounds (e.g, phenolic acids, flavonoids, coumarins), terpenoids, fatty acids, alkaloids and other functional components, which has the potential as a hypoglycemic drug (inhibiting α-glucosidase) substitutes (Papoutsis K, Zhang J, Bowyer M C, Brunton N, Gibney E R, Lyng J. Fruit, vegetables, and mushrooms for the preparation of extracts with α-amylase and α-glucosidase inhibition properties: A review. Food Chemistry, 2021, 338: 128119). However, grapefruit peel itself contains few active components and the activity is not strong. How to process pomelo peel and effectively enhance its biological activity has been paid more and more attention by researchers.

Fermentation is one of the effective ways to enhance plant-derived materials, edible and medicinal fungi can utilize the fiber, carbohydrate, protein and other substances in plant-derived materials during fermentation, wherein the enzymes produced have the effect of breaking the wall to dissolve the active ingredient, and may carry out biotransformation of ingredients in plant-derived materials to improve the efficacy of drugs. However, the effects of different strains of edible and medicinal fungi are very different, and the same strain of different strains that have completely different effects. Therefore, it is necessary to screen and invent a special strain for the fermentation of grapefruit peel to enhance its inhibition of α-glucosidase activity.

SUMMARY

In response to the problems of the existing technology, the present invention aims to design and provide a technical solution of an *Aspergillus oryzae* and its application.

The present invention is specifically realized by the following technical solutions:

The present invention, on the one hand, provides an *Aspergillus oryzae* (WZ-212), conserved at the China General Microbiological Culture Collection Center (CGMCC) on Nov. 10, 2021, address: Institute of Microbiology Chinese Academy of Sciences, NO. 1 West Beichen Road, Chaoyang District, Beijing 100101, China. The strain name is: WZ-212; the proposed taxonomic designation is *Aspergillus oryzae*; and the preservation number is: CGMCC No. 23295. The nucleotide ITS sequence of this *Aspergillus oryzae* is shown as SEQ ID NO:1. The present invention, on the other hand, provides this *Aspergillus oryzae* (WZ-212) in application of enhancing the inhibitory activity of α-glucosidase by grapefruit peel.

The present invention, on the other hand, provides a method for enhancing the inhibition of α-glucosidase activity by grapefruit peel with this *Aspergillus oryzae* (WZ-212).

Further, the method is using the *Aspergillus oryzae* (WZ-212) for liquid culture to obtain *Aspergillus oryzae* seed culture medium, and the *Aspergillus oryzae* seed culture medium was used for solid fermentation of grapefruit peel.

Further, the method specifically comprises the following steps:

(1) seed culture: inoculating spores of *Aspergillus oryzae* to a fresh seed culture medium for rotary deep fermentation of 2-3 days under a temperature of 28° C. and a speed of 170 r/min to obtain *Aspergillus oryzae* seed fluid, wherein the culture medium comprises: 200 g/L of soybean sprout, 20 g/L of glucose, 3-5 g/L of corn flour, 5-10 g/L of grapefruit peel; and (2) solid fermentation: smashing dry grapefruit peel and then passing the dry grapefruit peel through a 20 mesh sieve, weighing 100 g of grapefruit peel powder and placing it in a fermented container, adding distilled water to a water content of 60-80%, adding 2% of glucose and stirring well to sterilize at 121° C. for 30 min; adding 10-15% by volume mass ratio of *Aspergillus oryzae* seed solution after cooling, stirring well and leaving to ferment for 2-10 days at 26-34° C.

The beneficial effects of the present invention are:

The present invention isolated a strain of *Aspergillus oryzae* from naturally fermented Dendrobium *officinale* leaves, which was identified *Aspergillus oryzae* by reliable multiple identification methods, using this *Aspergillus oryzae* to treat grapefruit peel, the inhibition of α-glucosidase activity by grapefruit peel extract was significantly enhanced, and the process is simple, low cost, which is easy to achieve industrial production.

DESCRIPTION OF THE EMBODIMENTS

In order to make the purpose, technical solutions and advantages of the present invention clearer, the invention will be further described in detail in combination with the accompanying drawings.

For experimental methods without any indicated specific conditions, conventional methods and conditions may be preferred. Otherwise, a descriptive literature shall be used for reference upon selection.

The strain culture medium used in the following embodiment are as follows:

*Aspergillus oryzae* screening culture medium (g/L): 200 g/L of soybean sprout, 20 g/L of glucose, 15 g/L of agar, pH6.8 and 10 000 U of streptomycin;

Slant culture medium (g/L): 200 g/L of soybean sprout, 20 g/L of glucose, 15 g/L of agar, pH6.8;

Seed culture medium (g/L): 200 g/L of soybean sprout, 20 g/L of glucose, 5 g/L of corn flour, 10 g/L of grapefruit peel;

Embodiment 1: Screening Isolation and Identification of *Aspergillus oryzae* (WZ-212)

I. *Aspergillus oryzae* (WZ-212) was isolated from naturally fermented plant material (Dendrobium *officinale* leaves). Taking 10 g of naturally fermented samples, adding 50 mL of sterile normal saline and dilute it 10-5, 10-6, 10-7 times, taking 100 µL and coating on an *Aspergillus oryzae* screening medium plate and repeat each concentration 3 times, culturing at 28° C. for 72 hours, wherein the strain that produces spores is the mold; selecting spores for multiple purification, inoculating the purified strain onto slant culture medium, culturing at 28° C. for 72 hours and storing in 4° C. refrigerator for use.

Inoculating the strain which is stored at 4° C. refrigerator for use onto seed culture medium and culturing at 28° C. for 72 hours, then taking 10 mL of seed medium each and inoculating into 100 g of Dendrobium *officinale* leaves for fermentation, and measuring the fermentation matrix extract to inhibit the activity of α-glucosidase, from which a strain was selected with strong effect of enhancing the inhibition of α-glucosidase activity of Dendrobium *officinale* leaves and named as WZ-212.

II. Molecular Biological Identification of *Aspergillus oryzae* (WZ-212)

Culturing the target strain on slant culture medium for 72 hours, genomic DNA was extracted and ITS of the strain was amplified by PCR, the primers used are ITS1 ((SEQ ID NO: 2) 5'-TCCGTAGGTGAACCTGCGG-3') and

ITS4 ((SEQ ID NO: 3) 5'-TCCTCCGCTTATTGATATGC-3').

The composition of PCR reaction system is shown in the following table:

| Reagents | Volume(µL) |
|---|---|
| Template(genomic DNA 20-50 ng/µL) | 0.5 |
| 10 × Buffer(with $Mg^{2+}$) | 2.5 |
| dNTP(2.5 mM) | 1.0 |
| ITS1 primer(10 µM) | 0.5 |
| ITS4 primer(10 µM) | 0.5 |
| Tag enzymes | 0.2 |
| Double distilled water | 19.8 |

The PCR conditions are shown in the following table:

| Temperature | time | Procedures |
|---|---|---|
| 94° C. | 4 min | Predegeneration |
| 94° C. | 45 sec | 30 cycles |
| 55° C. | 45 sec | |
| 72° C. | 1 min | |
| 72° C. | 10 min | Repair extension |
| 4° C. | ∞ | Termination reaction |

Figure 1:
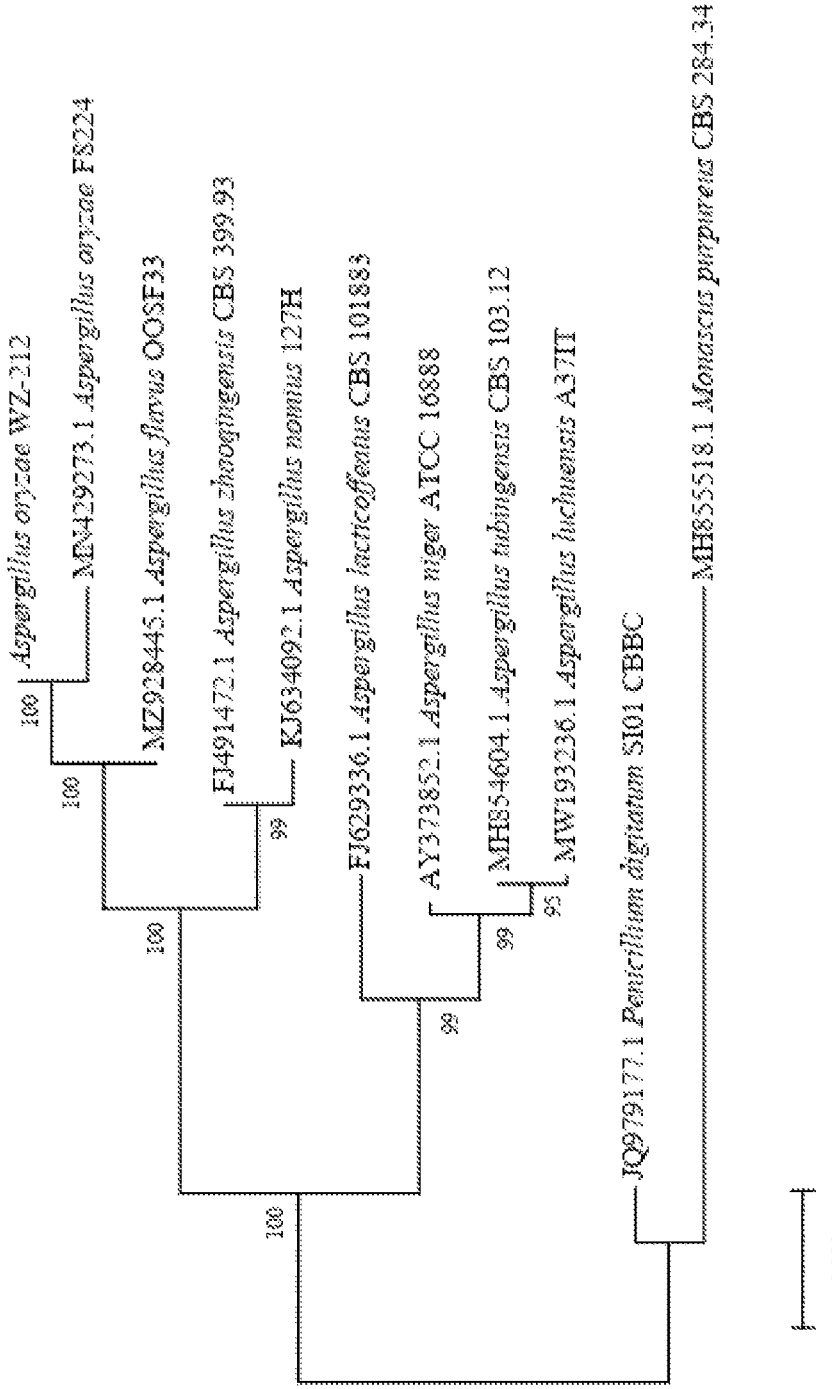
FIG. 1 The MEGA 7.0 software was used to display a phylogenetic tree of ITS sequence of strain CGMCC No. 23295 with related species in the GeneBank database with neighbor joining method.

PCR product was sequenced and the sequence was submitted to GeneBank database for homology comparison with ITS in GeneBank database, and the results are shown in FIG. 1. The highest homology with *Aspergillus oryzae* F8224 (GenBank accession No. MN429273.1) was found to be 100%. The strain was identified as *Aspergillus oryzae*, which was conserved at the China General Microbiological Culture Collection Center (CGMCC) on Nov. 10, 2021, with the preservation number: CGMCC No. 23295.

Embodiment 2: HPLC-MS Analysis of Compositional Changes of Grapefruit Peel Before and After Fermentation (1) Sample Processing Adding 5 g of sample to 100 mL of 80% ethanol solution, ultrasonic extracting at 50° C. for 120 min, centrifuging at 8000 r/min for 10 min, and collecting the supernate.

(2) Instrument and Determination Conditions

Ultra high performance liquid chromatography (U3000, Thermo Scientific) was combined with mass spectrometer (TripleTOF5600+, AB SCIEX).

Chromatographic conditions: Waters BEH C18 chromatographic column (150 mm×2.1 mm, 1.7 µm). Eluent, 0.1% formic acid (A) and acetonitrile (B). Gradient elute: 95% A for 0 min, 50% A for 10 min, 5% A for 15 min, 5% A for 17 min, 95% A for 20 min. The column temperature was 35° C., the flow rate was 0.3 mL/min, and the injection volume was 10 µL.

Mass spectrometry conditions: electron bombardment ion source (EI), the temperature of ion source was 500° C. (positive ions) and 450° C. (negative ions), the temperature of interface was 280° C., the scan mass range was 100 Da-1200 Da, and the fragment scan range was 50 Da-1200 Da.

(3) Data Processing

After the original data obtained by LC-MC was converted by Analysis Base File Converter, the data was processed by MS-Dial 4.60 software.

Embodiment 3: Determination of the Ability of Grapefruit Peel to Inhibit α-Glucosidase Activity (1) The Preparation of Sample and Reagent Weighing 0.5 g of grapefruit peel powder, adding 5 mL of 80% ethanol solution, ultrasonic extracting at 45° C. and 210 W for 45 min, centrifuging at 8000 r/min for 15 min, and collecting the supernate for use.

(2) Determination of the Ability to Inhibit the Activity of α-Glucosidase

Adding 3 mL of 0.1 mol/L phosphate buffer (pH 6.8) and 100μ of 1.625 U/mL α-glucosidase solution in turn according to the reaction system and mixed well, keeping warm in water bath at 37° C. for 10 min; removing and adding 200 μL of sample solution and 100μ of mmol/L PNPG (p-nitrobenzene-α-D-glucoside, 4-Nitrophenyl α-D-glucopyranoside) and mixed well, keeping warm in water bath at 37° C. for 10 min and adding 200 μL of 0.1 mol/L Na2CO3 solution quickly to terminate the reaction after the reaction, and determining the absorbance value (AS) at 405 nm. Under the same conditions, phosphoric buffer was used instead of sample solution to determine absorbance value (Ac), and enzyme solution was used instead of sample solution to determine absorbance value (Ab). The α-glucosidase inhibition ratio was calculated according to the following formula:

Inhibition ratio (%)=[Ac−(As−Ab)/Ac]×100%

Wherein: Ac: absorbance value of the control group; As: absorbance value of the sample group; Ab: absorbance value of the blank group.

At the same time, a standard curve was also prepared between acarbose concentration and the percentage of α-glucosidase inhibition, and the equivalent amount of acarbose activity (acarbose equivalent/g) per gram of grapefruit peel was calculated.

Embodiment 4

Figure 2:
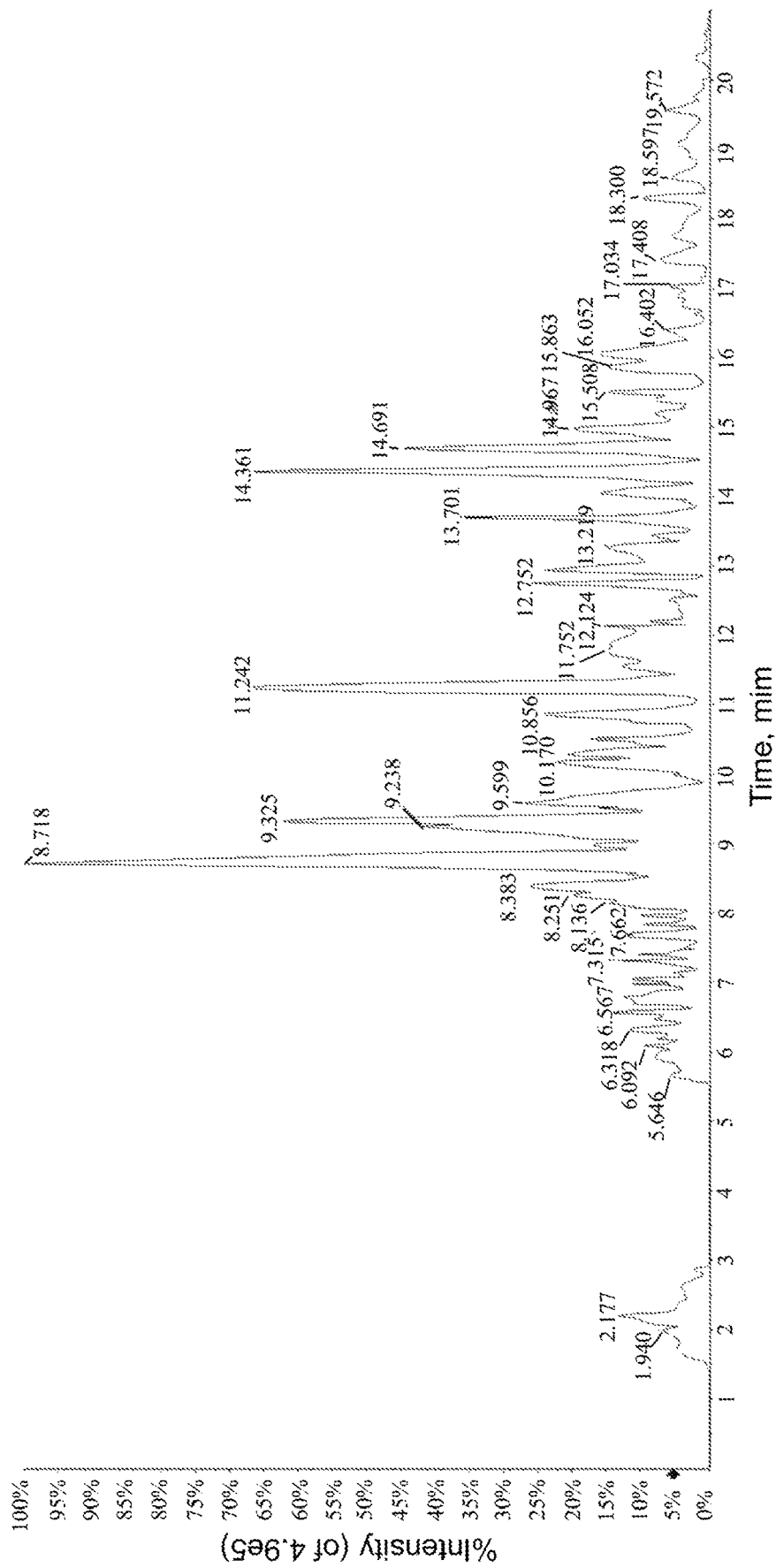
FIG. 2 HPLC-MS total ino flow diagram (positive ions) of grapefruit peel raw material.
Figure 3:
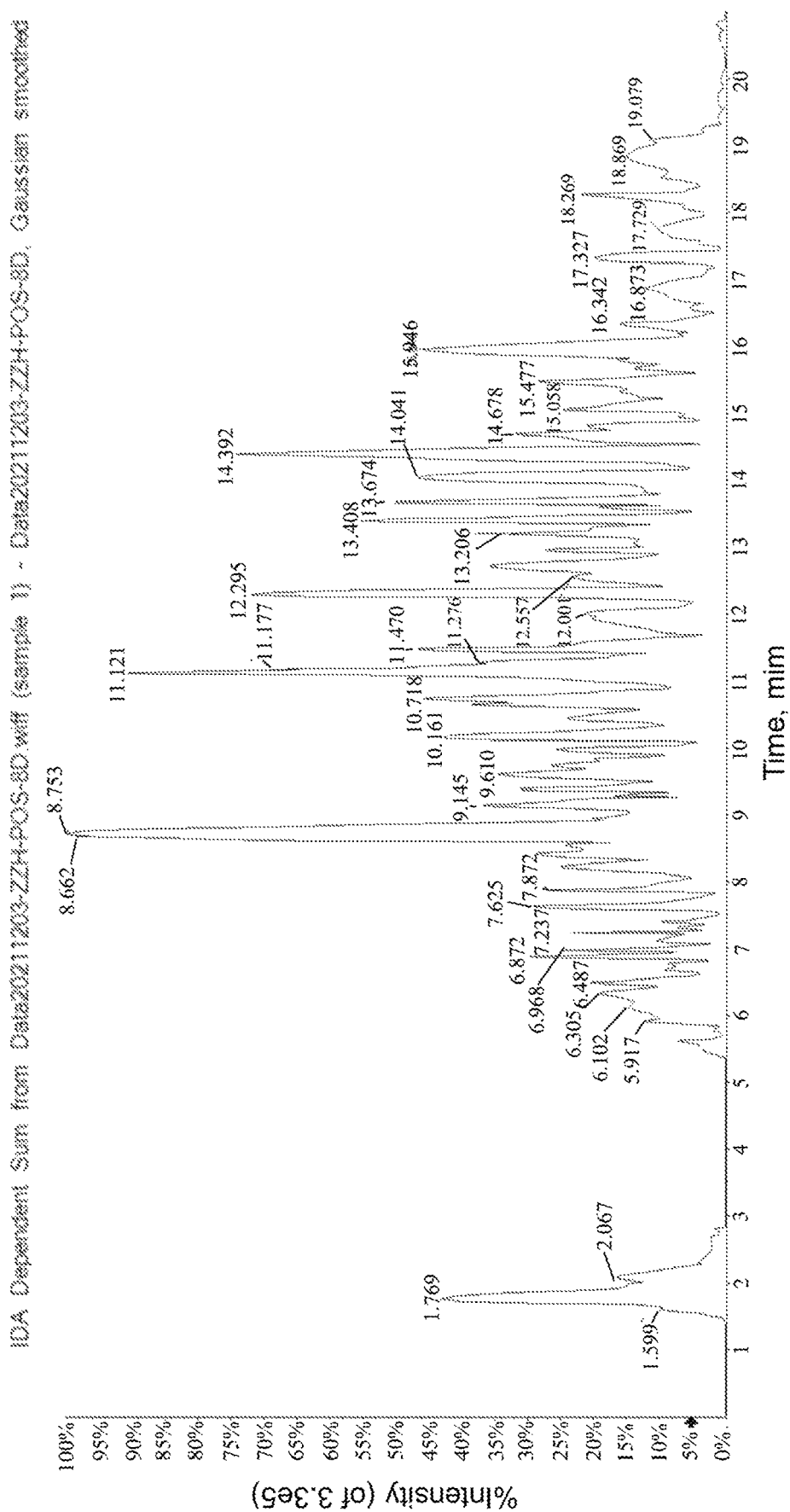
FIG. 3 HPLC-MS total ino flow diagram (positive ions) of the sample after fermentation of grapefruit peel by *Aspergillus oryzae* CGMCC No. 23295.

Inoculating *Aspergillus oryzae* CGMCC No. 23295 onto slant culture medium at 28° C. for 72 hours; then inoculating *Aspergillus oryzae* spores growing on the slant culture medium into fresh seed culture medium for rotary deep fermentation of 2-3 days under a temperature of 28° C. and a speed of 170 r/min to obtain *Aspergillus oryzae* seed solution; weighing 100 g of grapefruit peel powder and placing it in a fermented container, adding distilled water to a water content of 60%, adding 2% of glucose and stirring well to sterilize at 121° C. for 30 min; adding 10% by volume mass ratio of *Aspergillus oryzae* seed solution after cooling, stirring well and leaving to ferment for 8 days at 28° C. Taking grapefruit peel before and after fermentation for composition testing according to the method of Example 2, the total ino flow diagram of material components of grapefruit peel raw material and grapefruit peel extract after fermentation by *Aspergillus oryzae* is shown in FIG. 2 and FIG. 3. As can be seen from the figure, fermentation significantly changes the composition and content of grapefruit peel. The material components of grapefruit peel raw material and grapefruit peel extract after fermentation by *Aspergillus oryzae* are shown in Table 1. Determining the inhibition of α-glucosidase activity by samples according to the method of Example 3, and the results showed that the equivalent of sample acarbose increased from 1.11 mg/g to 8.98 mg/g.

TABLE 1

The material components of grapefruit peel raw material and grapefruit peel extract after fermentation by *Aspergillus oryzae*

| Serial number | retention time (min) | Compound | Relative content in raw materials (%) | Relative content after fermentation (%) |
|---|---|---|---|---|
| 1 | 1.815 | Benzoic acid | 0.0017 | 0.1428 |
| 2 | 2.342 | naringin | 13.9662 | 0.5990 |
| 3 | 4.901 | Vicenin | 36.3825 | 10.4230 |
| 4 | 5.901 | Naringenin chalcone | 1.1257 | 0.2784 |
| 5 | 5.901 | Troxerutin | 1.3545 | 0.0466 |
| 6 | 6.362 | Isovitexin | 0.5514 | 0.0379 |
| 7 | 6.379 | Vitexin | 0.2503 | 0.2997 |
| 8 | 6.619 | eriocitrin | 0.6412 | 1.2794 |
| 9 | 6.811 | 8-(2-hydroxy-3-methylbut-3-enyl)-7-methoxychromen-2-one | 0.7547 | 0.0131 |
| 10 | 6.998 | Rhoifolin | 0.5912 | 0.1396 |
| 11 | 7.092 | Narirutin | 0.0863 | 0.2342 |
| 12 | 7.111 | Genistein | 9.6763 | 8.3191 |
| 13 | 7.203 | naringenin-7-O-glucoside | 0.0619 | 1.8857 |
| 14 | 7.292 | Diosmetin | 0.3670 | 0.0791 |
| 15 | 7.659 | Naringenin | 1.0933 | 0.0304 |
| 16 | 8.252 | Ophiopogonoside A | 0.0326 | 0.2858 |
| 17 | 8.292 | Pectolinarin | 0.0053 | 0.0727 |
| 18 | 8.332 | Gaultherin | 0.0230 | 2.3389 |
| 19 | 8.53 | Phillyrin | 0.0072 | 0.2434 |
| 20 | 8.592 | Toddalolactone | 0.4911 | 0.0980 |
| 21 | 8.845 | Apigenin | 0.0276 | 5.1455 |
| 22 | 8.884 | Aloe-emodin | 0.0195 | 1.4520 |
| 23 | 8.965 | Kaempferol | 0.0068 | 1.2587 |
| 24 | 9.241 | Scopoletin | 0.0432 | 1.6289 |
| 25 | 9.281 | Psoralen | 0.0781 | 0.4727 |
| 26 | 9.281 | purpurin | 0.0576 | 11.7391 |
| 27 | 9.502 | Rotundine | 0.3999 | 0.0096 |
| 28 | 9.598 | Umbelliferone | 0.0532 | 0.1167 |
| 29 | 9.659 | Arctigenin | 0.7093 | 20.9781 |
| 30 | 9.677 | Secoxyloganin | 0.0002 | 1.2245 |
| 31 | 9.699 | Isoxanthohumol | 0.5714 | 0.0909 |
| 32 | 9.836 | hippeastrine | 0.0000 | 0.4319 |
| 33 | 10.217 | Cimifugin | 0.4525 | 0.0009 |
| 34 | 10.593 | 4',7-Di-O-methylnaringenin | 0.0155 | 0.1092 |
| 35 | 10.712 | 3'-hydroxygenkwanin | 0.0023 | 0.1694 |
| 36 | 10.809 | Citropen | 0.2473 | 0.0598 |
| 37 | 11.029 | Aloenin | 0.0002 | 0.2563 |
| 38 | 11.624 | Schizantherin E | 1.1520 | 0.6105 |
| 39 | 11.664 | Notopterol | 0.0602 | 0.2306 |
| 40 | 11.799 | Xanthohumol | 0.3169 | 0.0663 |
| 41 | 12.179 | Lucidenic acid D | 0.0005 | 0.4031 |
| 42 | 12.245 | 3,7-dimethyl-6-octenyl acetate | 0.8194 | 0.0009 |
| 43 | 12.258 | Lucidenic acid B | 0.0002 | 2.9080 |
| 44 | 12.298 | Stachydrine hydrochloride | 0.0010 | 0.3923 |
| 45 | 12.338 | NICOTINIC ACID | 0.0002 | 0.5780 |
| 46 | 12.338 | loganic acid | 0.1150 | 0.3034 |
| 47 | 12.402 | 6,8-Diprenylorobol | 0.2190 | 0.0013 |
| 48 | 12.595 | Benzoylgomisin O | 0.3463 | 0.6807 |
| 49 | 12.734 | Phytosphingosine | 0.0158 | 0.8410 |
| 50 | 12.774 | Lycorine hydrochloride | 0.0074 | 0.1550 |
| 51 | 12.947 | ostruthin | 13.5849 | 9.0129 |
| 52 | 13.208 | Hyoscine | 0.0001 | 0.0524 |

TABLE 1-continued

The material components of grapefruit peel raw material and grapefruit peel extract after fermentation by *Aspergillus oryzae*

| Serial number | retention time (min) | Compound | Relative content in raw materials (%) | Relative content after fermentation (%) |
|---|---|---|---|---|
| 53 | 13.293 | Bufotalin | 0.1511 | 0.0005 |
| 54 | 13.412 | 8-(2,3-dihydroxy-3-methylbutyl)-7-methoxychromen-2-one | 0.2197 | 0.0031 |
| 55 | 15.491 | Xanthotoxol | 1.3545 | 0.3995 |
| 56 | 16.226 | Liriopesides B | 0.0018 | 0.1653 |
| 57 | 16.825 | 9-Trans-Palmitelaidic acid | 0.0236 | 0.1214 |
| 58 | 16.989 | 4-hydroxy-7H-furo[3,2-g]chromen-7-one | 0.1698 | 0.0167 |
| 59 | 17.243 | 9Z,12Z-Linoleic acid (NMR) | 7.0809 | 7.2646 |
| 60 | 17.756 | Tetrahydrocoptisine | 0.0001 | 0.1344 |
| 61 | 18.164 | 20(R)-Protopanaxadiol | 0.4051 | 0.0998 |
| 62 | 18.232 | Indole-3-carbinol | 0.0016 | 0.4162 |
| 63 | 18.271 | Palmitic Acid | 1.3074 | 0.3658 |
| 64 | 18.47 | Oleic acid | 2.4665 | 2.7138 |
| 65 | 19.068 | Heptadecanoic acid | 0.0307 | 0.0717 |

Example 5

*Aspergillus oryzae* activation and seed preparation as in embodiment 4: weighing 100 g of grapefruit peel powder and placing it in a fermented container, adding distilled water to a water content of 60%, adding 2% of glucose and stirring well to sterilize at 121° C. for 30 min; adding 10% by volume mass ratio of *Aspergillus oryzae* seed solution after cooling, stirring well and leaving to ferment for 4 days at 28° C., the equivalent of acarbose increased from 1.11 mg/g of unfermented sample to 5.07 mg/g after fermentation.

Embodiment 6

*Aspergillus oryzae* activation and seed preparation as in embodiment 4: weighing 100 g of grapefruit peel powder and placing it in a fermented container, adding distilled water to a water content of 60%, adding 2% of glucose and stirring well to sterilize at 121° C. for 30 min; adding 10% by volume mass ratio of *Aspergillus oryzae* seed solution after cooling, stirring well and leaving to ferment for 6 days at 28° C., the equivalent of acarbose increased from 1.11 mg/g of unfermented sample to 6.01 mg/g after fermentation.

Embodiment 7

*Aspergillus oryzae* activation and seed preparation as in embodiment 4: weighing 100 g of grapefruit peel powder and placing it in a fermented container, adding distilled water to a water content of 60%, adding 2% of glucose and stirring well to sterilize at 121° C. for 30 min; adding 10% by volume mass ratio of *Aspergillus oryzae* seed solution after cooling, stirring well and leaving to ferment for 10 days at 28° C., the equivalent of acarbose increased from 1.11 mg/g of unfermented sample to 8.36 mg/g after fermentation.

What is claimed is:

1. A method for enhancing the inhibition of α-glucosidase activity by grapefruit peel with *Aspergillus oryzae* (WZ-212) comprising:
    performing liquid culture with the *Aspergillus oryzae* (WZ-212) with a preservation number of CGMCC No. 23295, to obtain *Aspergillus oryzae* seed culture medium; and
    adding the *Aspergillus oryzae* seed culture medium to grapefruit peel to perform solid fermentation.

2. The method of claim 1, characterized in that it comprises the following steps:
    (1) liquid culture: inoculating spores of *Aspergillus oryzae* with a preservation number of CGMCC No. 23295, to a fresh seed culture medium for rotary deep fermentation of 2-3 days under a temperature of 28° C. and a speed of 170 r/min to obtain an *Aspergillus oryzae* seed culture medium, wherein the culture medium comprises: 200 g/L of soybean sprout, 20 g/L of glucose, 3-5 g/L of corn flour, 5-10 g/L of grapefruit peel; and
    (2) solid fermentation: smashing dry grapefruit peel and then passing the dry grapefruit peel through a 20 mesh sieve, weighing 100 g of grapefruit peel powder and placing it in a fermented container, adding distilled water to a water content of 60-80%, adding 2% glucose and stirring well to sterilize at 121° C. for 30 min to obtain a grapefruit peel crude extract; adding 10-15% by volume mass ratio of the *Aspergillus oryzae* seed culture medium into the grapefruit peel crude extract after cooling the *Aspergillus oryzae* seed culture medium, stirring well and leaving to ferment for 2-10 days at 26-34° C.

\* \* \* \* \*

SEQUENCE LISTING

```
<160> NUMBER OF SEQ ID NOS: 3

<210> SEQ ID NO 1
<211> LENGTH: 506
<212> TYPE: DNA
<213> ORGANISM: Aspergillus oryzae WZ-212
<220> FEATURE:
<223> OTHER INFORMATION: Synthetic

<400> SEQUENCE: 1
ttctagcgag cccaacctcc cacccgtgtt tactgtacct tagttgcttc ggcgggcccg      60
ccattcatgg ccgccggggg ctctcagccc cgggcccgcg cccgccggag acaccacgaa     120
ctctgtctga tctagtgaag tctgagttga ttgtatcgca atcagttaaa actttcaaca     180
atggatctct tggttccggc atcgatgaag aacgcagcga aatgcgataa ctagtgtgaa     240
ttgcagaatt ccgtgaatca tcgagtcttt gaacgcacat tgcgcccct ggtattccgg      300 ggggcatgcc tgtccgagcg tcattgctgc ccatcaagca cggcttgtgt gttgggtcgt     360
cgtcccctct ccggggggga cgggcccaa aggcagcggc ggcaccgcgt ccgatcctcg      420
agcgtatggg gctttgtcac ccgctctgta ggcccggccg gcgcttgccg aacgcaaatc     480
aatcttttcc aggtgacctc ggatca                                          506

<210> SEQ ID NO 2
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 2
tccgtaggtg aacctgcgg                                              19

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tcctccgctt attgatatgc                                             20
```